United States Patent
Auvray et al.

(10) Patent No.: US 11,545,252 B2
(45) Date of Patent: Jan. 3, 2023

(54) MEDICAL REPORTING APPARATUS

(71) Applicant: KONINKLIJKE PHILIPS N.V., Eindhoven (NL)

(72) Inventors: Vincent Maurice André Auvray, Meudon (FR); Romane Isabelle Marie-Bernard Gauriau, Paris (FR); Raoul Florent, Ville D'Avray (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 72 days.

(21) Appl. No.: 16/066,334

(22) PCT Filed: Dec. 20, 2016

(86) PCT No.: PCT/EP2016/081833
§ 371 (c)(1),
(2) Date: Jun. 27, 2018

(87) PCT Pub. No.: WO2017/114685
PCT Pub. Date: Jul. 6, 2017

(65) Prior Publication Data
US 2019/0019579 A1 Jan. 17, 2019

(30) Foreign Application Priority Data
Dec. 30, 2015 (EP) .................................. 15307181

(51) Int. Cl.
*G16H 30/20* (2018.01)
*G16H 15/00* (2018.01)
(Continued)

(52) U.S. Cl.
CPC ............. *G16H 30/20* (2018.01); *A61B 6/481* (2013.01); *A61B 6/504* (2013.01); *G16H 15/00* (2018.01);
(Continued)

(58) Field of Classification Search
CPC ........ G16H 30/40; G16H 15/00; G16H 10/60; A61B 6/481; A61B 6/504; A61B 6/468; G06F 19/321
See application file for complete search history.

(56) References Cited

U.S. PATENT DOCUMENTS

| | | | |
|---|---|---|---|
| 5,095,906 A | * | 3/1992 | Ema ........................ G06T 5/50 378/98.12 |
| 2007/0064987 A1 | * | 3/2007 | Esham .................. A61B 6/481 382/128 |

(Continued)

OTHER PUBLICATIONS

Sanborn, Timothy et al. "Health Policy Statement on Structured Reporting for the Cardiac Catheterization Laboratory" American Quality Committee, Journal of the American College of Cardiology, vol. 63, No. 23, 2014.

(Continued)

*Primary Examiner* — Zhitong Chen (57) ABSTRACT

During a medical intervention such as an angiography, the X-ray examination equipment (such as that mounted on a C-arm) produces a very large number of imaging frames of the intervention, as it progresses. This information contains frame sequences which can be effectively used to improve a medical report of the intervention. The sequence will contain sequences which contain similar clinical information though, and these frames may be considered to be redundant and not useful for inclusion in the medical report. The aspects detailed herein enable a selection of non-redundant sequences and/or frames, based on contextual information, obtained from the sequence of images, and/or other medical equipment, during an intervention. In this way, the redundancy inherent in the original frame sequence can be removed, leaving a set of prepared candidate sequences for insertion into a multimedia or documentary medical report.

18 Claims, 6 Drawing Sheets

(51) Int. Cl.
*G16H 30/40* (2018.01)
*A61B 6/00* (2006.01)
*G16H 10/60* (2018.01)

(52) U.S. Cl.
CPC .............. *G16H 30/40* (2018.01); *A61B 6/468* (2013.01); *G16H 10/60* (2018.01)

(56) References Cited

U.S. PATENT DOCUMENTS

| | | | |
|---|---|---|---|
| 2010/0210945 A1* | 8/2010 | Zhang | A61B 6/466 600/443 |
| 2011/0238082 A1* | 9/2011 | Wenderow | A61M 25/0105 606/130 |
| 2015/0126860 A1* | 5/2015 | Beymer | A61B 6/468 600/431 |
| 2015/0223769 A1 | 8/2015 | Imagawa | |
| 2018/0078226 A1* | 3/2018 | Helm | A61B 6/4405 |

OTHER PUBLICATIONS

Auvray et al "Improved Vessel Enhancement for Fully Automatic Coronary Modeling", SPIE Proceedings, vol. 7259, Medical Imaging 2009.

Gavio, Wilson et al "Hysteroscopy Video Summarization and Browsing by Estimating the Physicians Attention on Video Segments", Medical Image Analysis, vol. 16, No. 1, Jun. 2011.

Buecker, A. et al "Simultaneous Real-Time Visualization of the Catheter Tip and Vascular Anatomy for MR-Guided PTA of Iliac Arteries in an Animal Model", Journal of Magnetic Resonance Imaging, Society for Magnetic Resonance Imaging, vol. 16, No. 2, Jan. 2002, pp. 201-208.

Zhu, Xingquan et al "ClassMiner: Mining Medical Video Content Structure and Events towards Efficient Access and Scalable Skimming", Retrieved from the Internet: URL:https://www.cs.purdue.edu/homes/ake/pub/dmkd02.pdf. 2016.

Bredno, J. et al Algorithmic Solutions for Live Device-to-Vessel Match, Proceedings of SPIE, vol. 5370, Medical Imaging, 2004, pp. 1486-1497.

* cited by examiner

MEDICAL REPORTING APPARATUS

CROSS-REFERENCE TO PRIOR APPLICATIONS

This application is the U.S. National Phase application under 35 U.S.C. § 371 of International Application No. PCT/EP2016/081833, filed on Dec. 20, 2016, which claims the benefit of European Patent Application No. 15307181.6, filed on Dec. 30, 2015. These applications are hereby incorporated by reference herein.

FIELD OF THE INVENTION

The present invention relates to an apparatus for computer-aided medical report provision, a method for computer-aided medical report provision, a system configured for medical reporting, a computer program element, and computer readable medium.

BACKGROUND OF THE INVENTION

A medical intervention, such as an angiography, involves a wide range of diagnostic and interventional steps. It is important that these steps are documented properly in the form of a medical report. An intuitive way of presenting results in a report is in a graphical format. However, in the time-intensive context of a catheterization laboratory, it can be difficult for a medical professional to download and extract from imaging equipment images bearing useful information. In addition, some clinical information can only be conveyed in a dynamic format, and it is even more labour-intensive to manually edit the corresponding videos.

Therefore, post-intervention clinical reports do not often contain as much multimedia or imaging content as would be desirable.

The document "Health Policy Statement on Structured Reporting for the Cardiac Catheterization Laboratory", a report of the American Quality Committee, by Sanborn et al., published in the Journal of the American College of Cardiology, vol. 63, no. 23, 2014, ISSN 0735-1097 discusses issues surrounding medical reporting.

SUMMARY OF THE INVENTION

It would, thus, be advantageous to have technique for providing improved intra-procedural reporting during medical procedures.

The object of the present invention is solved by the subject-matter of the independent claims, wherein further embodiments are incorporated in the dependent claims.

These and other aspects of the present invention will become apparent from, and be elucidated with reference to, the embodiments described hereinafter.

According to a first aspect of the invention, there is provided an apparatus for computer-aided medical report provision. The apparatus comprises:

a processing unit.

The processing unit is configured to receive a sequence of frames obtained from a medical imaging device. The frames represent a region of interest of a patient. The processing unit is further configured to generate contextual information derived from an input from an item of medical equipment.

The processing unit is configured to index frames of the sequence of frames to the contextual information. The processing unit is configured to generate at least one representative subset of the frames of the sequence of frames, wherein the frames of the at least one representative subset are selected from the sequence of frames by comparing the contextual information of frames of the sequence of frames to at least one frame clustering condition.

The processing unit is configured to select at least one further subset of the frames of the at least one representative subset using a selection parameter defined for the at least one representative subset, and to output a multimedia or documentary report comprising the further subset of frames.

An effect of the first aspect is that the high information content of an input frame sequence obtained during a medical intervention may be reduced automatically, by omitting frames, and/or frame subsets, that are likely to contain redundant information of a medical intervention, such as a catheterization. The process of assembling a multimedia or documentary report is, therefore, simplified.

According to an embodiment of the first aspect, the processor is further configured to receive orientation information of the item of medical imaging equipment, wherein the contextual information comprises the orientation information, and wherein the frame clustering condition comprises an orientation condition.

An effect of this embodiment is that the selection of frame sequences may be further enhanced using information about the orientation of the equipment used to obtain the medical images, is typically highly correlated with the image content.

According to an embodiment of the first aspect, the apparatus is provided as described above. The processor is further configured to receive an event signal comprising information about an event linked to the stage of a medical procedure, and to generate a procedure status indication using the event signal. The contextual information further comprises the procedure status indication, and frames of the at least one representative subset are selected from the sequence of frames based on the procedure status indication, and the at least one frame clustering condition.

An effect of this embodiment is that the stage of a medical procedure may be inferred based on an external stimulus.

According to an embodiment of the first aspect, in the apparatus according to the previous description, the event signal is a balloon inflation state signal.

An effect of this embodiment is that the status of a medical procedure may be tracked by identifying balloon inflation events of a balloon.

According to an embodiment of the first aspect, the processor is further configured to receive a measurement device activity parameter from output signals of a patient monitoring device, wherein the contextual information further comprises the measurement device activity parameter. The frames of the at least one representative subset are selected based on the presence of the measurement device activity parameter, and the multimedia or documentary report comprises a measurement from the measurement equipment displayed in proximity to the further subset of frames.

An effect of this embodiment is that the provision of frame sub sequences, or medical images, in association with relevant medical report information, is simplified.

According to an embodiment of the first aspect, the processor is further configured to classify frames of the sequence of frames by identifying a specific artery system represented in the frames, thereby providing frames of the sequence of frames with an artery system classification. The contextual information further comprises the artery system classification, wherein the frame clustering condition comprises an artery system classification parameter. The frames of the at least one representative subset are selected based on a comparison of the artery system classification of each frame with the artery system parameter.

An effect of this embodiment is that, when the orientation of the medical equipment does not change, the movement of a catheter from one arterial branch to another may be detected. This prevents the erroneous creation of report sequences or images, where, for instance, the right and left coronary branches, observed from the same orientation, would erroneously be considered to be an examination of the same arterial branch. This avoids the risk of the generation of an incomplete summary, in which relevant sequences showing the left or right coronary branches from different perspectives would be ignored.

According to an embodiment of the first aspect, the processor is further configured to compute a contrast agent quality metric for a plurality of frames of the at least one representative subset of the frames. The selection parameter is an injection quality parameter, and the frames of the at least one further subset of the frames are selected based on a comparison of the contrast agent quality metric and the injection quality parameter.

An effect of this embodiment is that the amount of redundant information in a reported further subset, may be further reduced by ensuring that only good quality injected images are present in the further subset of images, or by selecting the well-injected images, along with subsequent images, over a given duration. This means that muscle-blood perfusion, subsequent to the contrast agent injection, may be documented effectively. In the case where the further subset is one image, the image having the best contrast agent quality is selected.

Another effect of this embodiment is that, when the at least one representative subset comprises different sequences clustered together, for example, with frames taken from the same imaging system orientation, the same artery system, and the same exam stage, the further subset can be reduced to the most well-injected of these images.

According to an embodiment of the first aspect, the processor is further configured to compute a balloon inflation progress metric for a plurality of frames of the at least one representative subset of the frames. The selection parameter is a balloon inflation extent metric, and the frames of the at least one further subset of the frames are selected based on a comparison of the balloon inflation progress metric and the balloon inflation extent metric.

An effect of this embodiment is that the redundant information content of a reported frame video sequence may be further reduced by ensuring that only frames with a relevant balloon inflation state are displayed in a multimedia or documentary report, in the case of the acquisition of a series of sequences corresponding to a succession of balloon inflations.

Optionally, the processing unit is further configured to generate contextual information derived from (i) the sequence of frames and (ii) an input from an item of medical equipment.

According to a second aspect of the invention, there is provided a method for computer-aided medical report provision. The method comprises the following steps:
a) receiving a sequence of frames, obtained from a medical imaging device, representing a region of interest of a patient;
b) generating contextual information derived an input from an item of medical equipment;
   wherein the frames of the sequence of frames are indexed to the contextual information;
c) generating at least one representative subset of the frames of the sequence of frames,
   wherein the frames of the at least one representative subset are selected from the sequence of frames by comparing the contextual information of frames of the sequence of frames to at least one frame clustering condition;
d) selecting at least one further subset of the frames of the at least one representative subset using a selection parameter defined for the at least one representative subset; and
e) outputting a multimedia or documentary report comprising the further subset of frames.

An effect of the second aspect is that a multimedia or documentary report of a medical procedure may be provided containing a reduced (or zero) number of redundant frames, whilst retaining frames having clinical significance. Therefore, the data size of a multimedia or documentary report can be reduced, whilst retaining useful images. The time of medical professionals producing the report is also saved, because a sequence of images does not need to be searched manually.

According to an embodiment of the second aspect, the method further comprises:
a1) receiving orientation information of the item of medical imaging equipment;
   wherein in step b), the contextual information comprises the orientation information; and
   wherein in step c), the frame clustering condition comprises an orientation condition.

According to an embodiment of the second aspect, a method as discussed previously is provided, further comprising the steps of:
a2) receiving an event signal comprising information about an event linked to the stage of a medical procedure;
b1) generating a procedure status indication using the event signal;
   and wherein, in step c), the frames of the at least one representative subset are selected from the sequence of frames based on a combination of the procedure status indication, and the at least one frame clustering condition.

According to an embodiment of the second aspect, the method further comprises:
c1) computing a contrast agent quality metric for a plurality of frames of the at least one representative subset of the frames;
   wherein in step d), the selection parameter is an injection quality parameter, and the frames of the at least one further subset of the frames are selected based on a comparison of the contrast agent quality metric and the injection quality parameter.

According to a third aspect of the invention, there is provided a system configured for medical reporting. The system comprises:
   a medical imaging system;
   an apparatus according to the second aspect or its embodiments, and
   a display arrangement.

The medical imaging system is configured to generate a sequence of frames, and the apparatus is communicatively coupled to the medical imaging system and the display arrangement. In operation, the apparatus receives the sequence of frames from the medical imaging system, and outputs a multimedia or documentary report comprising a subset of frames of the sequence of frames.

According to a fourth aspect of the invention, there is provided a computer program element for medical reporting, comprising instructions which, when the computer program element is executed by a processing unit, is adapted to perform the method steps according to the second aspect, or one of its embodiments.

According to a fifth aspect of the invention, there is provided a computer readable medium having stored the computer program element of the fourth aspect.

In the following description, the term "computer-aided medical report provision" means the at least partly automated provision of a document (or multimedia presentation) for the attention of a medical professional which succinctly summarizes the key events of a medical intervention using video sequences, and/or still images, obtained by a medical imaging device, such as an X-ray fluoroscopy device or angiography device. The video sequences contain little or no redundant information.

In the following description, the term "orientation information" refers to a spatial context of a medical examination, such as a cardiac catheterization. In practice, it is information allowing the direction of view of an item of imaging equipment through a region of interest of a patient to be ascertained. For example, the orientation information may be the azimuth and elevation angles of a C-arm imaging system. Such signals can be obtained from electronic position control signals of the C-arm, or alternatively may be calculated based on an image processing algorithm applied to image content of the input sequence of images.

In the following description, the term "artery system classification" refers to a state of a model of an artery system that tracks which branch of an arterial system is being examined with interventional equipment. For example, at a constant orientation, the view of the region of interest may involve a catheter entering a left coronary branch, and then a right coronary branch, with an angiography being performed in both branches. Such a situation gives rise to different clinical information, even at a constant orientation. Therefore, an artery branch under investigation may be tracked using, for example, a ridge filter, to identify a relevant arterial branch under examination.

In the following description, the term "procedure status indication" refers to a time-based context of a medical examination. A simple example is that a balloon inflation is an event signal which can be used to classify an input sequence into a pre-intervention sub-sequence, and a post-intervention sub-sequence. A plurality of such inflations can partition an input image sequence into a plurality of sub-sequences, each characterizing a unique stage of an intervention.

In the following description, the term "contextual information" means stimuli available from equipment commonly available in a catheterization laboratory which may be used, alone or in ensemble, to provide information about the frames of an input sequence in medical imaging.

In an example, the contextual information may be an ensemble of (i) orientation information and (ii) a procedure status indication. However, many other such signals will be available, based on the particular setup of a catheterization laboratory, and all may be used to provide contextual information.

A "frame clustering condition" is a property that a plurality of contiguous frames in the sequence of frames have in common, allowing the sequence of frames to be decomposed into frame clusters which represent different stages of an intervention. A wide variety of stimuli can be used to generate the frame clustering condition, such as medical imaging equipment orientation. It enables a grouping of frames of the sequence of frames showing the same view (for example, the same artery branch, shown at the same orientation).

The procedure status indication enables a separation of the input frame sequence based on the contextual information. Thus, redundant information can be removed from the input frame sequence. An example of redundant information is when several angiograms are made of the heart, each from the same orientation, in the same arterial branch, and at the same stage of a procedure. Only one of these sequences needs to be saved, and the rest are redundant.

In the following description, the term "representative subset" means a subset of frames of the input sequence which share a common contextual information state, wherein the common contextual information state is not duplicated amongst further representative subsets.

In the following description, the term "further subset" means a subset of frames of the representative subset which have been selected for optimal presentation of the event captured in frames of the representative subset. In an example concerning an angiography, the further subset could be one frame of a representative subset showing the frame with the highest quality contrast burst. In another example, the further subset could be a sequence of frames showing a brief release of contrast agent which accurately summarizes fluid flow in a blood vessel. In another example, the further subset could be a frame of the representative subset showing a balloon at its maximum inflation, or just after its deflation, to enable the placement of a stent to be accurately summarized and reported.

In the following description, the term "contrast agent quality metric" refers to a measure of how much contrast agent is visible in a frame. Shortly after contrast injection, a vessel may be saturated (100% contrast agent presence). After a few seconds, diffusion of the contrast agent may be such that only wisps of the contrast agent are visible in the lumen. In this second case, not enough lumen detail can be discerned, and so this state may be assigned a 10% contrast agent presence. This metric may be calculated using well-known image processing techniques.

In the following description, the term "injection quality parameter" refers to the quality of the distribution of contrast agent in a lumen. For example, a bad quality injection can optionally be classified as one in which a "streak" of contrast agent appears in the lumen. No lumen shape information can reliably be observed from such a "streak". For example, a spatial image filter can be used to determine the presence of such "streaks".

In the following description, the term "selection parameter" means a variable that enables the selection of a frame or series of frames in the further subset of frames. It will be appreciated that there are many events that could impact the choice of such frames. A first example is the monitoring of the extent of the inflation of an intravascular balloon during stenting. In this case, the selection parameter is a percentage of the balloon inflation extent, determined from the video, or from hardware signals (such as pressure) obtained from the medical equipment. Frames may be entered into the "further subset" when the balloon inflation is in the range of 90 to 100 percent. A second example of the selection parameter is the density of contrast medium injected into a lumen. Frames may be entered into the "further subset" starting with a time instant at the point of release of contrast medium, and ending when a diffusion of the contrast medium is detected.

In the following description, the term "artery system classification parameter" refers to tracking an interventional device in an arterial tree. In a simple example, the artery system classification parameter may refer to the "left branch" or the "right branch" of the coronary artery tree.

The technique discussed is applicable at least to an input frame sequence capturing an angiography, and a fluoroscopy. In the case of angiography, redundant frames are considered at least to include those sub-sequences showing the same orientation, artery system classification, and procedure status, for example. In the case of fluoroscopy sub-sequences, most frames of the input sequence of frames will be redundant, apart from occasional "key images" of ballooning operations and outcomes, optionally presented along with the relevant measurements.

Therefore, a simplified explanation is that a range of stimulus signals providing information about the overall context of a catheterization enable the isolation of a first set of frames from an input sequence of frames. This may best be thought of as a "clustering step", whereby sequences are grouped based on, for example, the examination phase (diagnosis, intervention, outcome control) and the acquisition conditions (system geometry, and/or the artery system under examination). Then, a further selection can be made for image relevance, in a "prototyping step" that consists, for each cluster, of designating a good-quality subset of frames representing that cluster—for example, the "best injected angiogram". The output of the groups, and their prototypes, can be exploited to provide a concise summary of the intervention. Thus, the described technique proposes to select, automatically, medical image sequences, such as X-ray sequences, that are relevant for documenting certain aspects of an intervention, whilst removing redundant frames.

BRIEF DESCRIPTION OF THE DRAWINGS

Exemplary embodiments of the invention will be described with reference to the following drawings.

DETAILED DESCRIPTION OF EMBODIMENTS

An important follow-up to a medical intervention is to provide a report detailing important stages of the exam. Modern medical imaging equipment provides a large number of frames throughout the length of a medical intervention. The present situation is that the output of medical imaging devices is combined with the reports much less than should be the case.

A potential reason for this could be that it is repetitive, and time consuming, for a medical professional to search through a large body of images, for suitable illustrations to summarize an entire medical procedure. Reports may also be presented as multimedia presentations (such as intranet web pages), enabling the use of video clips. However, loading the sequence of an entire intervention into video editing equipment to find suitable frames is cumbersome.

The non-inclusion of short video clips in multimedia reports is a lost opportunity. Qualitative phenomena, for example, the blood flow in arteries, and through suspected stenoses, as well as the blood perfusion into the myocardium, are arguably well characterised using a dynamic angiogram sequence.

The discussion in the following description focuses on the situation of producing multimedia or documentary reports of PTCA (Percutaneous Transluminal Coronary Angioplasty) for treating coronary stenoses, where medical videos would be obtained of the procedure using a C-arm having X-ray imaging equipment. The technique is applicable to many other medical video imaging scenarios, such as an endoscopy of the throat, stomach, or lungs, Trans Aortic Vascular Interventions (TAVI), and neurological interventions though.

A typical angiogram typically lasts between 5 and 20 seconds, and the imaging equipment may provide images of a vasculature at between 1 and 150 frames per second (typically 15). This means that a single typical angiography typically contains 75 frames.

A typical intervention involves about ten angiographies, and in addition, sequences of fluoroscopy images lasting between 10 and 30 seconds can be produced. The number of frames to be searched rapidly builds up. This makes a manual search of the frames time-consuming. In addition, many of the angiography sequences are taken from the same orientation. Such multiple sequences taken from the same orientation can be considered to be "redundant", because they contain the same anatomy information as a first angiography taken from that orientation, provided the clinical condition of the patient has not been modified between their acquisitions. The clinical condition could be modified by the deployment of a stent using a balloon, for example. The deletion of such redundant frames is desirable.

Another kind of redundancy arises in relation to the quality of sequences of non-redundant frames. Once the redundant frames have been removed, an angiography sequence will contain frames which do not show blood vessels sharply, owing to an incomplete diffusion of contrast agent. Such empty angiograms are, typically, not useful in a medical report. Therefore, the size of a reported sequence can be further compressed by selecting non-redundant angiogram frames with good vessel boundary properties, for example.

The variety of technical equipment present in a modern catheter laboratory presents an opportunity, because such equipment is usually digitized, and constantly provides digital outputs and updates via open communication interfaces. As a medical intervention progresses, the outputs from these items of technical equipment will change, in a way that enables a context about the stage of a medical procedure to be inferred automatically. This information can be used to remove the redundant images from an intervention.

Figure 1:
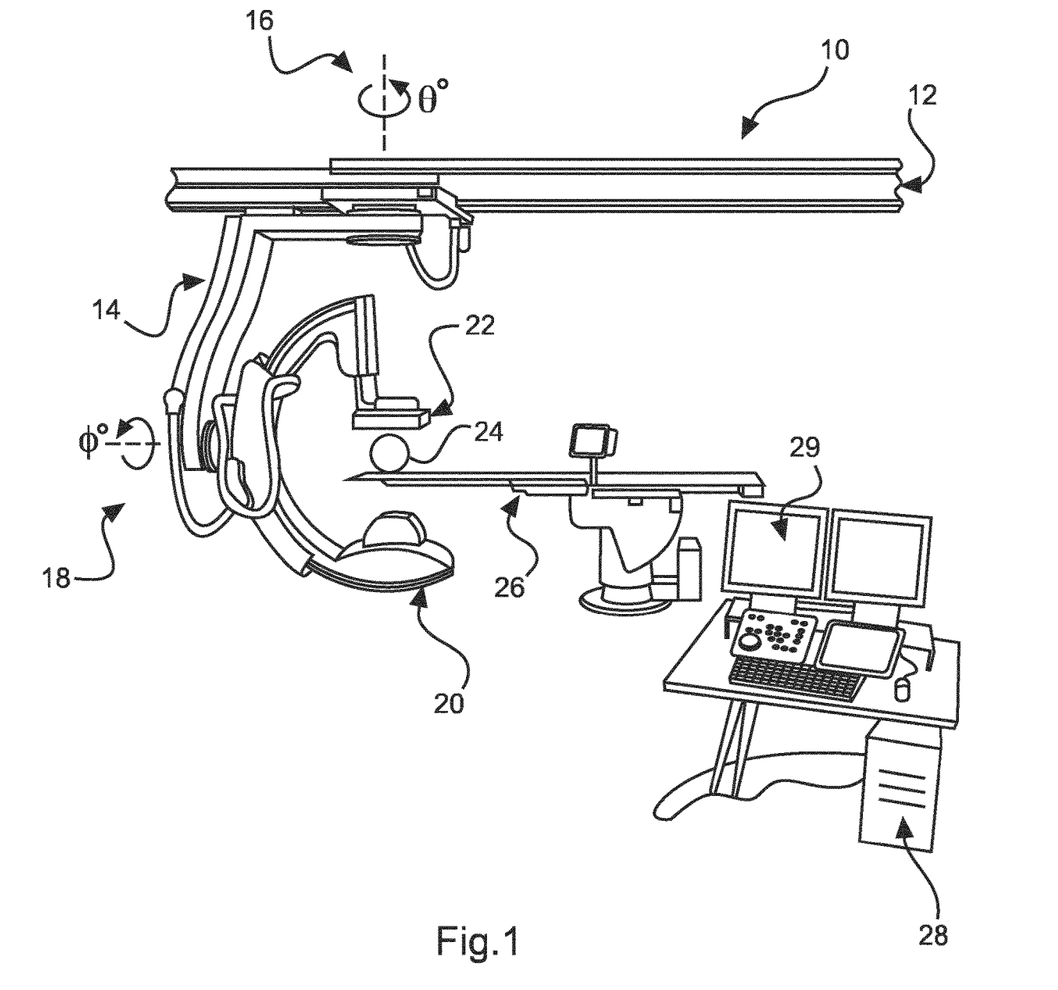
FIG. 1 shows a system configured for medical reporting according to a third aspect.

FIG. 1 illustrates a catheter laboratory 10. It comprises a ceiling rail 12 supporting a C-arm 14. The C-arm comprises an X-ray source 20 and detector 22 arranged to image a region of interest of an object 24 (such as a patient) supported on a bed 26. Bearings of the C-arm enable the C-arm, and thus the detector and source, to be moved through an azimuth angle θ and an elevation angle (I). The angulations of the C-arm may be tracked electronically by monitoring C-arm position control signals sent from a C-arm control apparatus. The position control signals, providing C-arm orientation information, may be provided to a processing unit 28 for further use. This information can act as contextual information of a medical intervention.

The X-ray detector 22 of the C-arm detects X-rays applied to an item in the region of interest 24 as frames of an X-ray imaging sequence. These frames may be collected and recorded using a processor 28, and stored for further use.

A catheterization laboratory also contains other items of equipment useful for providing contextual information. Although these items are not illustrated in FIG. 1, such items may provide signals indicating that a contrast agent is being injected into a patient amongst many other signals. These signals may be supplied as contextual information. Certain measurement techniques, such as, for example, a fractional flow reserve measurement (FFR), an optical coherence tomography (OCT) and an intravascular ultrasound (IVUS) may be deployed at specific moments of an intervention, providing more contextual information about the stage of the medical procedure. All of this information may be collected by a processing apparatus 28 through appropriate electronic interfaces, and indexed in time to the frames output by the X-ray detector.

Figure 2:
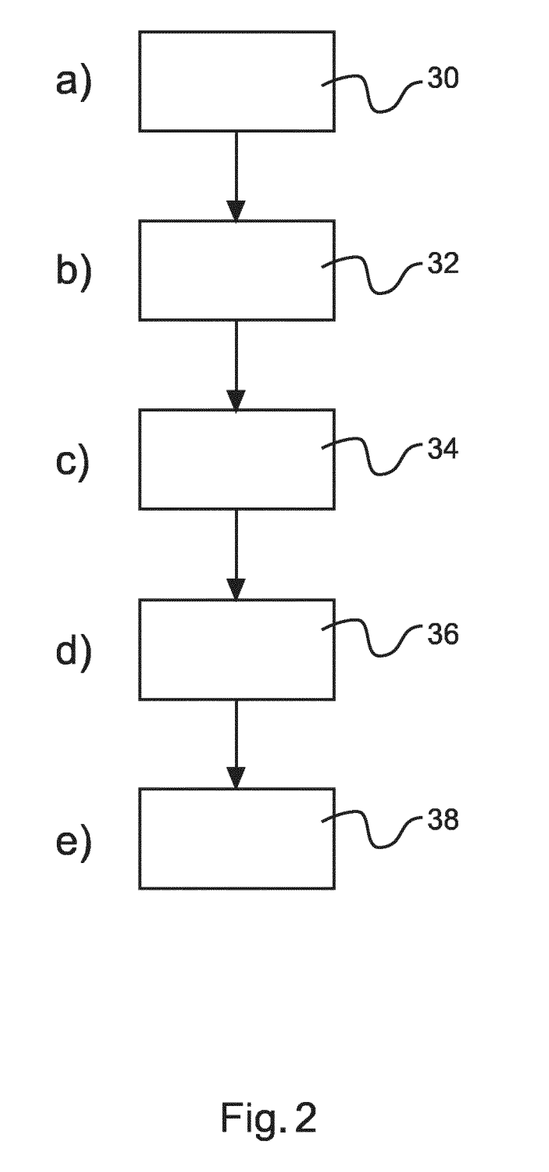
FIG. 2 shows a method for computer-aided medical report provision, according to a second aspect.

FIG. 2 shows a method for computer-aided medical report provision according to a second aspect of the invention. The method comprises the steps of:
a) receiving (30) a sequence of frames, obtained from a medical imaging device, representing a region of interest of a patient;
b) generating (32) contextual information derived from an input from an item of medical equipment;
wherein the frames of the sequence of frames are indexed to the contextual information;
c) generating (34) at least one representative subset of the frames of the sequence of frames,
wherein the frames of the at least one representative subset are selected from the sequence of frames by comparing the contextual information of frames of the sequence of frames to at least one frame clustering condition;
d) selecting (36) at least one further subset of the frames of the at least one representative subset using a selection parameter defined for the at least one representative subset; and
e) outputting (38) a multimedia or documentary report comprising the further subset of frames.

An effect is that an input sequence of images may be filtered so as to remove redundant image sequences, leaving only sequences containing unique information and/or images having clinical importance. The resulting shorter sequence and/or set of still images may then be forwarded to create a multimedia or documentary report. As another consideration, the total memory needed to store the images and/or videos used in the report is thereby reduced significantly, enabling a medical intervention to be efficiently recorded.

Figure 3:
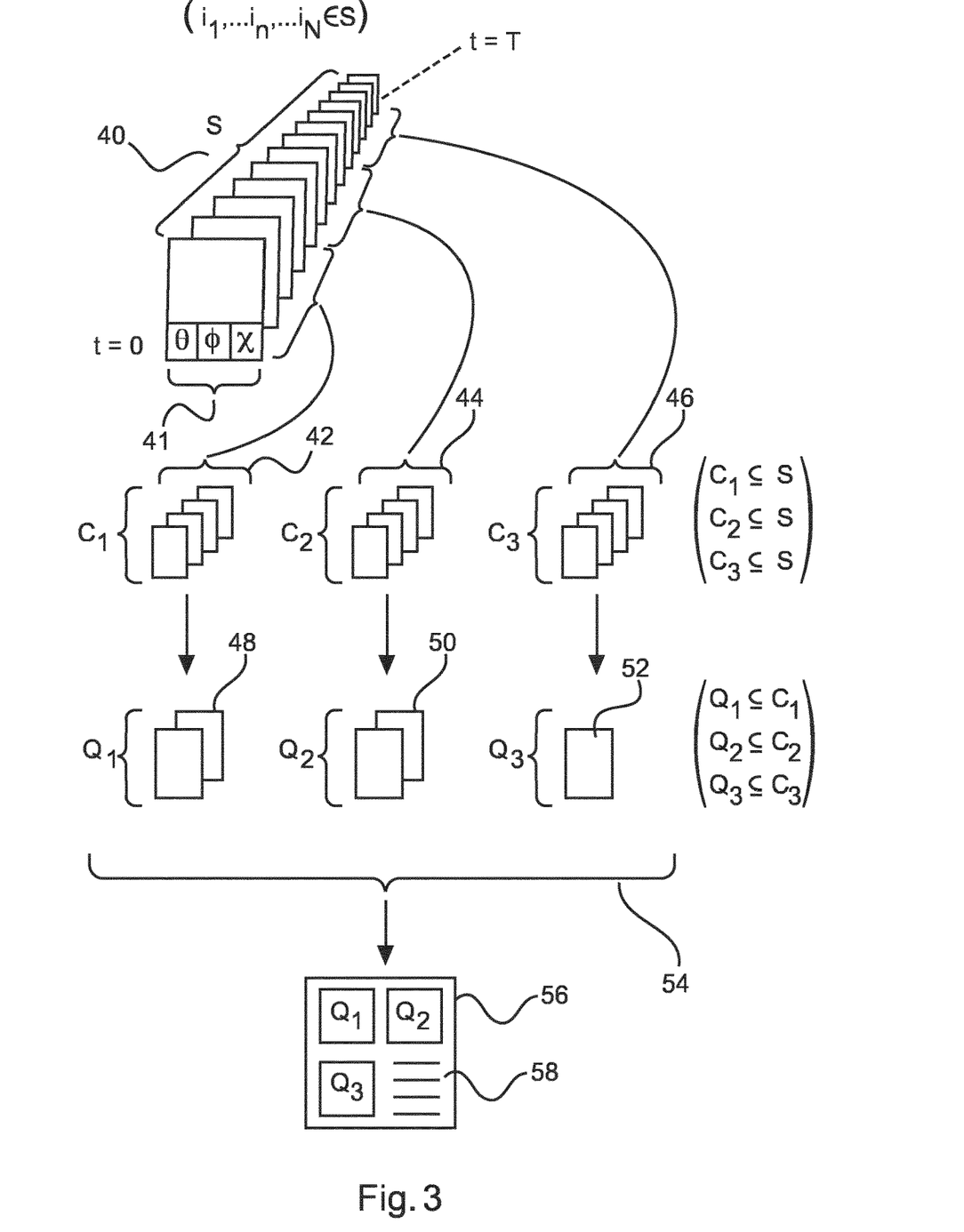
FIG. 3 shows a summary of the functioning of the redundancy-reduction approach employed according to aspects discussed.

FIG. 3 illustrates the overall operation of the second aspect. The method may be implemented in, for example, a personal computer or other suitable processing apparatus. The method may run "live" on the stream of images and contextual information, or alternatively may be stored on a data carrier, or transferred over a computer network, and run "offline" on a remote computer.

In FIG. 3, there is illustrated a sequence S of frames 40 which, when played in sequence, provide a video of an imaged medical procedure, such as a series of angiographic sequences and/or a fluoroscopic sequence concatenated together. The frames are recorded over the time interval t=0 to t=T. The collection frequency of the sequence need not be regular, because an angiography process may be performed at a high or a low frequency to control the exposure of a patient to X-rays. The received frames form a set S having members $(i_j, \ldots, i_n, \ldots i_N, \in S)$. Contextual information 41 is provided which enables a selection of a representative subset of frames to be made. In this example, the contextual information includes the time-dependent orientation information $(\theta(t), \phi(t))$ indexed to each frame of the input sequence, and a procedure status parameter x(t).

In the example of FIG. 3, the input sequence has been divided into a first representative subset 42 of diagnostic frames $C_1$, a second representative subset 44 of intervention frames $C_2$, and a third representative subset 46 of outcome control frames $C_3$. It will be appreciated that many sets of representative frames for any stage of an intervention could be generated. $C_1$, $C_2$, and $C_3$ may be non-overlapping subsets of S—in other words, if a frame appears in $C_1$, then it will not appear in other subsets of representative frames (as shown in the notation in FIG. 3).

Alternatively, one or more of $C_1$, $C_2$, and $C_3$ may be overlapping subsets of S.

First representative subset $C_1$ has been derived using orientation information $(\theta(t), \phi(t))$ comprised in the contextual information, at a first procedure status x(1). Second representative subset $C_2$ has been derived based on contextual information comprising a second procedure status x(2). Third representative subset $C_3$ has been derived based contextual information comprising a third procedure status x(3). The orientation between $C_1$, $C_2$, and $C_3$ usually changes.

In the case illustrated in FIG. 3, the first, second, and third representative subsets are used to generate first 48, second 50, and third 52 further subsets, yielding output sequences (or frames) $Q_1$, $Q_2$, and $Q_3$. The selection of frames of each further subset may be based on the same, or different selection parameters.

The choice of selection parameter can be optimized to each particular representative subset. If representative subsets $C_1$ and $C_3$ refer to angiography sequences, frames of $Q_1$ and $Q_3$ may be selected as first and second further subsets based on the best-quality contrast agent burst of a frame, or a number of frames, in the first and second representative subsets, for example. Contrast agent bursts are frequently used in diagnostic and outcome-control sequences.

Alternatively, representative subset $C_2$ is a frame of a fluoroscopy sequence. In this case, the frame of the third further subset $Q_2$ has been selected based on an event signal, such as a balloon inflation signal, for example, to document a single frame showing the deployment of a stent.

The selected first, second, and third subsets may be output in the form of a multimedia report 56, such as a Microsoft PowerPoint(™) presentation, a proprietary secured intranet or secured internet portal, or another format enabling viewing of the first, second and third further subsets. In the case that the first, second and third further subsets have been assembled to constitute one frame each, the report could be output in the form of a documentary report, where the subset frames are static images, for example, in portable document format(™). Relevant clinical information may be provided next to the report 58.

According to an embodiment, the frame clustering condition identifies unique combinations of the contextual information.

Optionally, the contextual information is derived from (i) the sequence of frames, and/or (ii) an input from an item of medical equipment.

Optionally, the contextual information is data received from a data output of item of medical equipment.

Optionally, the sequence of frames is obtained from a single video source, so that the sequence of frames is a continuous uninterrupted sequence.

According to an embodiment of the second aspect, the method according to the second aspect is provided, further comprising the step a1):

a1) receiving orientation information of an item of medical imaging equipment;
wherein in step b), the contextual information comprises the orientation information; and
wherein in step c), the frame clustering condition comprises an orientation condition.

In an embodiment, the orientation information is derived from the orientation signals of a C-arm medical imaging system.

The derivation may be made, for example, using a classical unsupervised clustering. This refers to a case where an algorithm automatically identifies the groups that are present in the quadrants of the azimuth and elevation space of the C-arm. The goal is to provide an algorithm that finds clusters (identified by their centres) that (i) minimize the distance of the points to the corresponding cluster centres and (ii) avoids introducing too many clusters. An example of algorithm that performs this task, for a given number of clusters k, is via the "k-means" algorithm. The complete solution would, for example, to extract 2, 3, . . . 10 clusters, and select the combination that gives the best compromise between points (i) and (ii).

Thus, the clustering parameters would be a compromise between the method of computation, and the number of tested clusters.

In an embodiment, the orientation information is derived using an image processing algorithm applied to the frames of the sequence of frames representing a region of interest of a patient.

A suitable orientation condition could be classical unsupervised clustering.

According to an embodiment of the second aspect, a method according is provided as discussed above, further comprising:

a2) receiving an event signal comprising information about an event linked to the stage of a medical procedure;
b1) generating a procedure status indication using the event signal;
and wherein, in step c), the contextual information further comprises the procedure status indication, and wherein frames of the at least one representative subset are selected from the sequence of frames based on the procedure status indication, and the at least one frame clustering condition.

In an example, the procedure status signal is generated by counting the number of event signals which occur. For example, the procedure status signal may indicate a diagnosis phase of a procedure, inferred from the fact that no event signals have occurred.

The procedure status signal may indicate that an intervention phase is underway after a first event signal is received. It will be appreciated that a plurality of event signals can be received, with each subsequent event signal dividing the input frame sequence into sub-sequences representing none of a plurality of interventions.

According to an example, the procedure status may indicate that an outcome control phase is in progress if no new event is observed.

Therefore, according to the present embodiment, the contextual information is a composite of at least a procedure status indication, and orientation information, and optionally the artery classification.

According to an embodiment, the event signal is a balloon inflation signal from a balloon inflation catheter system.

In an example, the balloon inflation signal is provided from an item of equipment used to inflate the balloon. In another example, the balloon inflation signal is provided by detecting a balloon inflation using image processing techniques applied to the input sequence of images.

Therefore, an event, such as a balloon inflation, is used to enhance the search for redundant frames. According to this embodiment, it is possible to identify a procedure status indication from the event signals.

Thus, according to this embodiment it is possible to separate the stages of an intervention procedure by detecting balloon inflations. Applying the frame clustering condition in combination with the procedure status indication, it is possible, for example, to identify a plurality of sub-sequences of the input sequence of frames sharing the same orientation (of the imaging system) and the same procedure status indication. In this case, all but one of the plurality of redundant sub-sequences can be removed, thus reducing the number of redundant frames.

According to an embodiment, the method as discussed previously is provided, further comprising the step of:

a3) classifying frames of the sequence of frames by identifying a specific artery system represented in the frames, thereby providing frames of the sequence of frames with an artery system classification;
wherein in step b), the contextual information further comprises the artery system classification; and
wherein in step c), the frame clustering condition comprises an artery system classification parameter, and wherein frames of the at least one representative subset are selected based on a comparison of the artery system classification of each frame with the artery system parameter.

According to an embodiment, the artery system classification parameter provides a left coronary artery and a right coronary artery classification using a ridge filter.

A simple illustrative example of a situation where the contextual information comprises orientation information, artery side information, and procedure status information is presented in Table 1.

TABLE 1

| | Orientation information ($\theta_N$, $\phi_N$) | Artery side (L/R) | Procedure status (1 = before balloon, 2 = after balloon) | Keep subset? (Y/N) |
|---|---|---|---|---|
| 1. | ($\theta_1$, $\phi_1$) | L | 1 | Y |
| 2. | ($\theta_2$, $\phi_2$) | L | 1 | Y |
| 3. | ($\theta_3$, $\phi_4$) | L | 1 | Y |
| 4. | ($\theta_4$, $\phi_4$) | L | 1 | Y |
| 5. | ($\theta_1$, $\phi_1$) | R | 1 | Y |
| 6. | ($\theta_1$, $\phi_1$) | L | 1 | N |
| 7. | ($\theta_1$, $\phi_1$) | L | 2 | Y |
| 8. | ($\theta_2$, $\phi_2$) | L | 2 | Y |

In Table 1, each row of the table represents an angiography examination involving a contrast burst, and so each row of the table a sub-sequence of the input frame sequence, indexed to contextual information. In this example, contextual information is provided as orientation information (azimuth and elevation of a C-arm performing the imaging), a detected artery side (for example, the left or right coronary tree, detection of which may be achieved using a ridge filter applied to input frames), and a procedure status indication, in terms of whether the stage is before (1) or after (2) an event signal—in this case, a balloon deployment.

A frame clustering condition is provided which identifies unique combinations of the contextual information.

In Table 1, rows 1 to 4 represent a clinician searching for a stenosis on the left artery side at different angulations ($\theta_1$, $\phi_1$) to ($\theta_4$, $\phi_4$). The search process is carried out before any balloon inflation. At row 5, the clinician has changed the catheter from the right heart branch to the left heart branch to perform a diagnostic angiography on the right heart branch.

It should be noted that the orientation information may be ($\theta_1$, $\phi_1$), i.e. the orientation information is the same at row 1 is the same as at row 5, even though a different clinical outcome (different anatomy and/or stenosis condition of the right and left heart branches) is observed.

At row 6, the clinician has, seemingly, found nothing worthy of subsequent investigation in the right heart branch, and returns to an orientation ($\theta_1$, $\phi_1$), with the catheter in the left heart branch, which appeared to contain a treatable stenosis.

At row 7, a balloon is deployed, to inflate a stent, used for treatment of the stenosis. Thus, at row 7, the exam stage changes from "1" to "2".

At row 8, the orientation information changes to ($\theta_2$, $\phi_2$), because the clinician is verifying the placement of a stent from a different angle, with the angiography still taking place in the left coronary branch.

Thus, rows 1 to 5 are diagnosis phases of the exam. Row 7 is an intervention phase. Row 8 is an outcome control phase.

In the simple example of Table 1, a balloon inflation signal would be used to generate a procedure status indication having two states (before and after a balloon inflation), although a large plurality of balloon inflations may be accommodated.

Applying a frame clustering parameter which identifies unique combinations of the contextual information, it is clear that the subset of frames of row 6 may be deleted, because these will contain the same redundant image information as the subset of frames of row 1 (an angiography of the left branch taken at an orientation of ($\theta_1$, $\phi_1$), before balloon inflation).

Thus, out of the 8 basic divisions of the input frame sequence, 7 representative subsets, each representing a cluster of frames with different contextual information, may be provided. These representative subsets are processed as further subsets, to further remove redundancies from the selected angiography sequences.

According to an embodiment, the method according the above embodiments is provided, further comprising the step a3):
a3) receiving a measurement device activity parameter from output signals of a patient monitoring device;
wherein in step b), the contextual information further comprises the measurement device activity parameter;
wherein in step c), the frames of the at least one representative subset are selected based on the presence of the measurement device activity parameter; and
wherein in step e), the multimedia or documentary report comprises a measurement of the output signals of a patient monitoring device displayed in proximity to the further subset of frames.

Accordingly, a representative subset may be captured at the same time as useful medical information from other monitoring equipment, such as a fractional flow reserve (FFR) measurement, is being collected. This affords the opportunity to present a video or image of a medical intervention, alongside relevant measurements.

According to an embodiment, the method as described above is provided, further comprising the step a4) of:
a4) receiving a balloon inflation state signal;
wherein in step b), the contextual information further comprises the balloon inflation state signal; and
wherein in step c), the frames of the at least one representative subset are selected based on a state of the balloon inflation state signal.

According to an example, the frames of the at least one representative subset are selected based on the state of the balloon inflation state signal, and the temporal proximity of the frames to the balloon inflation state signal.

According to an embodiment, the balloon inflation state signal is received from a balloon inflation control device.

According to an embodiment, the balloon inflation state signal is generated using an image processing algorithm which assesses the overall inflation of the balloon by analyzing frames of the sequence of frames.

According to an embodiment, the balloon inflation state signal is generated when the balloon is at its maximum inflation, or immediately after deflation. Alternatively, the signal may be generated throughout the period of balloon inflation, enabling the entire balloon inflation and deflation sequence to be captured.

According to an embodiment, the method as discussed previously is provided, further comprising in step c):
c1) computing a contrast agent quality metric for a plurality of frames of the at least one representative subset of the frames;
wherein in step d), the selection parameter is an injection quality parameter, and the frames of the at least one further subset of the frames are selected based on a comparison of the contrast agent quality metric and the injection quality parameter.

In one embodiment, the selection is based on an algorithm which provides the further subset of frames, based on an identification of the hardest edges, using an edge filter.

In another embodiment, the selection is based on an algorithm which provides the further subset of frames showing the largest extent of contrast agent in the frame or frames by area of the frame covered by contrast agent.

In another embodiment, the selection is based on an algorithm which provides the further subset of frames in which the contrast agent propagates furthest along a given arterial path.

According to an embodiment, the method as discussed previously is provided, further comprising in step c):
c2) computing a balloon inflation progress metric for a plurality of frames of the at least one representative subset of the frames;
wherein in step d), the selection parameter is a balloon inflation extent metric, and the frames of the at least one further subset of the frames are selected based on a comparison of the balloon inflation progress metric and the balloon inflation extent metric.

According to the second aspect, or any of the above-described embodiments, the input sequence of frames may be derived from an item of medical imaging equipment selected from the group: angiography equipment, fluoroscopy equipment, endoscope, medical ultrasound imaging, thermograph, echocardiograph, functional near-red spectroscopy, or conventional video.

According to an embodiment, a user-operated input (such as a push-button, pedal switch, etc) may provide the contextual information.

This enables a medical professional to provide a signal indicating that when a user-operated input was activated, frames recorded for the duration of the user-operated input activation should be stored as a representative subset. This enables unexpected moments of medical interest identifiable by a medical professional during an intervention to be saved as a representative subset, for presentation in a report.

According to an embodiment, the method according to the second aspect may receive the sequence of frames obtained from a medical imaging device indirectly. For example, the sequence of frames may be stored by a medical imaging device onto a data carrier such as a DVD, USB stick, or a portable hard drive. Alternatively, the data may be transmitted over a LAN, or WAN. The sequence of frames may be received by a processing device such as a personal computer, for example, and processed "offline". In addition, the contextual information indexed to the sequence of frames may be provided along with the sequence of frames obtained from a medical imaging device, to enable offline processing to occur according to the above-discussed method.

Figure 4:
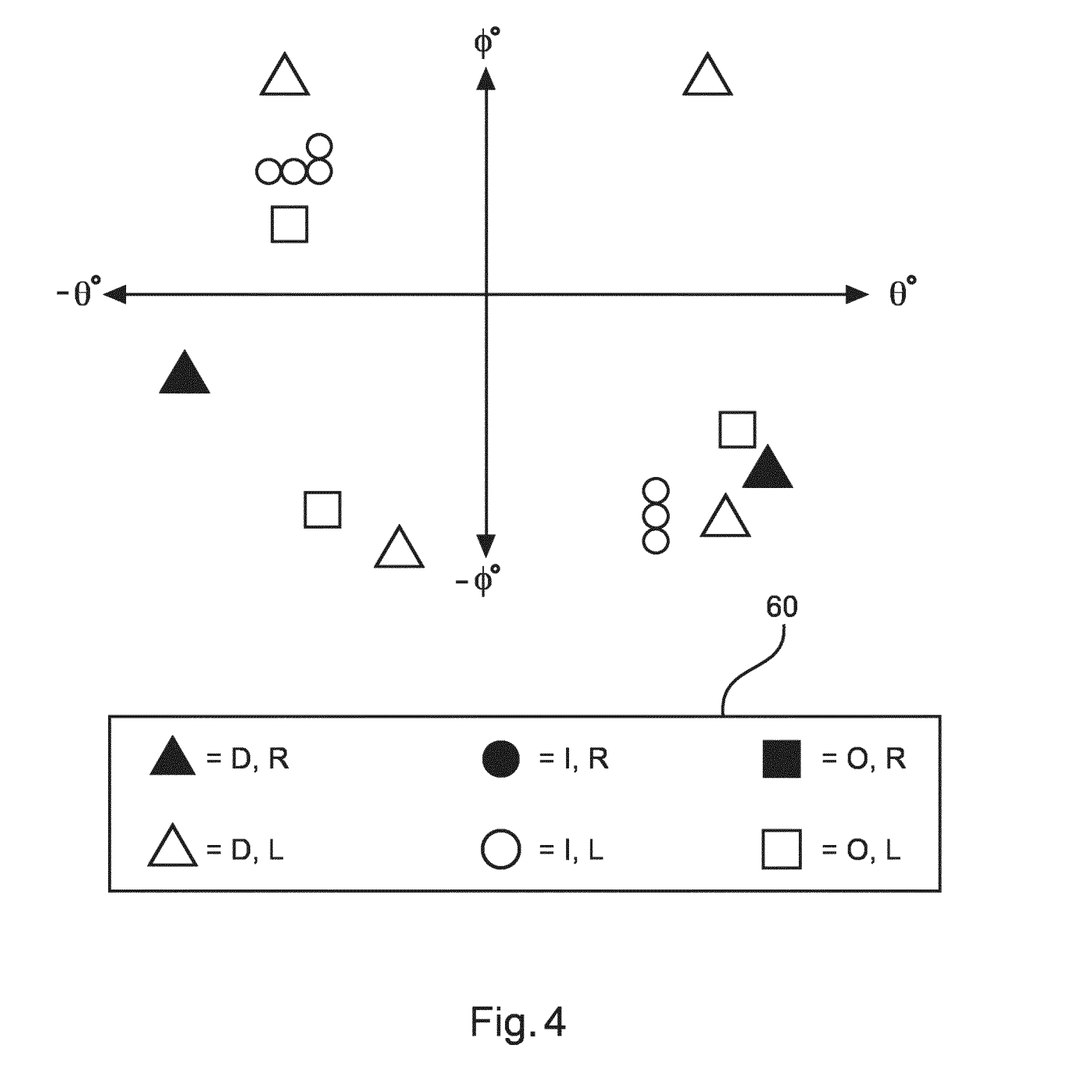
FIG. 4 shows the "orientation space" of a typical medical intervention using a C-arm.

FIG. 4 shows a representation of measurements made in C-arm space for a typical intervention. The θ axis represents the azimuth angle (rotation), and the φ axis represents the elevation axis (angulation) over a range of angles experienced for a typical patient intervention.

To further illustrate the operation of the second aspect, a specific example is presented with reference to FIG. 4, in the context of a cardiovascular intervention.

Initially, a clinician will image the heart of the patient, using different C-arm angulations, from a series of different perspectives, enabling a fine understanding of the geometry of the coronary arteries to be obtained. This task is performed for the right and the left coronary tree. The result is a series of long, well-injected diagnostic sequences, which are well-separated in C-arm angulation space.

Once a decision has been taken to treat a specific lesion, specific angulations are chosen which allow a clear view onto the lesion (so that there is no vessel clutter, and little foreshortening). This enables a guide-wire to be navigated past the stenosis, allowing a balloon, and stents, to be positioned over it.

In terms of the contextual information that is obtained from the process, several clusters of sequences of frames are obtained in C-arm space, mostly of interest as a unique record of an intervention. These sequences can have a useful diagnostic value, if they are well-injected, because they focus on the lesions.

Finally, a series of angiographic sequences are acquired from different reference views, in order to control the outcome of the intervention. Their signature in C-arm space is similar to that of the initial diagnostic sequences.

In this diagram, the key 60 illustrates different points of a diagnostic sequence. The solid triangle is a diagnostic view on the right coronary artery side. The unfilled triangle represents a diagnostic view on the left coronary artery side. The solid circle represents an intervention on the right coronary artery side, and the open circle denotes an intervention on the left coronary artery side. Finally, the solid square represents a control run on the right coronary artery side, and the open square represents a control run on the left coronary artery side.

Thus, in FIG. 4, a clinician has observed the right coronary from two different angulations, and then decided that no treatment is needed. The left coronary tree has been diagnosed from four angulations, which resulted in a stenosis being found. A decision to treat was made. A "spider view" (Left anterior oblique (LAO) caudal view) used to delineate the left main coronary artery and the proximal region of major branches is taken (illustrated in the bottom right quadrant). The guide wire was navigated proximally, and the navigation was finished from a cranial RAO view (in the left top quadrant). A control of the stent positioning was then made from three different positions.

Sequences acquired from a similar C-arm angulation provide the same kind of information about the geometry of the coronaries, provided no interventions have been carried out between views. An exception to this rule is when a change of artery tree from the right to left coronary artery trees is made, or vice-versa. These branches can be acquired from the same angulation, but contain clinical information which should not be merged. Therefore, and as discussed above, embodiments enable coronary branch information to be used to avoid the merging of this clinical content. In this case, the contextual information comprises at least the C-arm orientation information, and the artery tree classification. An artery tree can be classified, for example, using ridge filters. Ridge filters are further discussed in the paper "improved vessel enhancement for fully automatic coronary modeling", by Auvray et. al, published in SPIE Proceedings Vol. 7259, Medical Imaging 2009: Image Processing, doi: 10.1117/12.810144.

The evaluation of the quality of an injection enables barely injected sequences to be discarded. When selecting a sequence to represent one cluster (representative subset), choosing the best injected image may make sense, to make the clinical content of such an image more visible. In technical terms, the injection quality can be estimated by computing the cumulative number of ridges in the sequence, for example, although other techniques may also be applicable.

When balloon inflation equipment is used in an intervention, the detection of balloon inflations enables the structuring of an intervention into pre-dilation, intervention, and post-dilation.

According to an embodiment, each representative sequence is labeled according to the detection of a balloon inflation. This may be implemented by recognizing, using image processing techniques, a balloon signature—a non-injected sequence presenting a contrasted elongated object between two markers, for example.

Inputs from measuring tools allow local measurements and analysis to be added to the examination. Of course, the X-ray sequences used to position, and to pull-back these tools, are of little interest for reporting, except to document which branch is being analyzed. Therefore, according to an embodiment, the timing of measurements may be indexed to frames of the sequence of frames. The measurement timing information may also be comprised in the contextual information, to enable frames likely to concern measurement tool positioning to be discarded.

Advantageously, an approach as outlined above enables the relevant medical sequences to be obtained:

Diagnosis: sufficiently well-injected angiography, isolated in the C-arm angulation space, before a balloon inflation is performed; A best injected angiography before a balloon inflation, when considering a cluster in the C-arm angulation space, and an FFR, IVUS, and OCT result of the examined centerline, before a balloon inflation is performed in the relevant branch.

Intervention: A series of ballooning may be performed, enabling corresponding pre and post angiography sequences to be isolated.

Outcome control: Sufficiently well injected angiographies, isolated in the C-arm angulation space, after balloon may be provided. Sequences of best-injected angiographies after balloon inflation, when considering a cluster in the C-arm angulation space. Finally, a FFR, IVUS, and OCT result may be provided, after a balloon has been expanded in the relevant branch.

The selection of frames of the further subset is intended to ensure that frames of the representative having good enough quality for reporting are provided.

Figure 5:
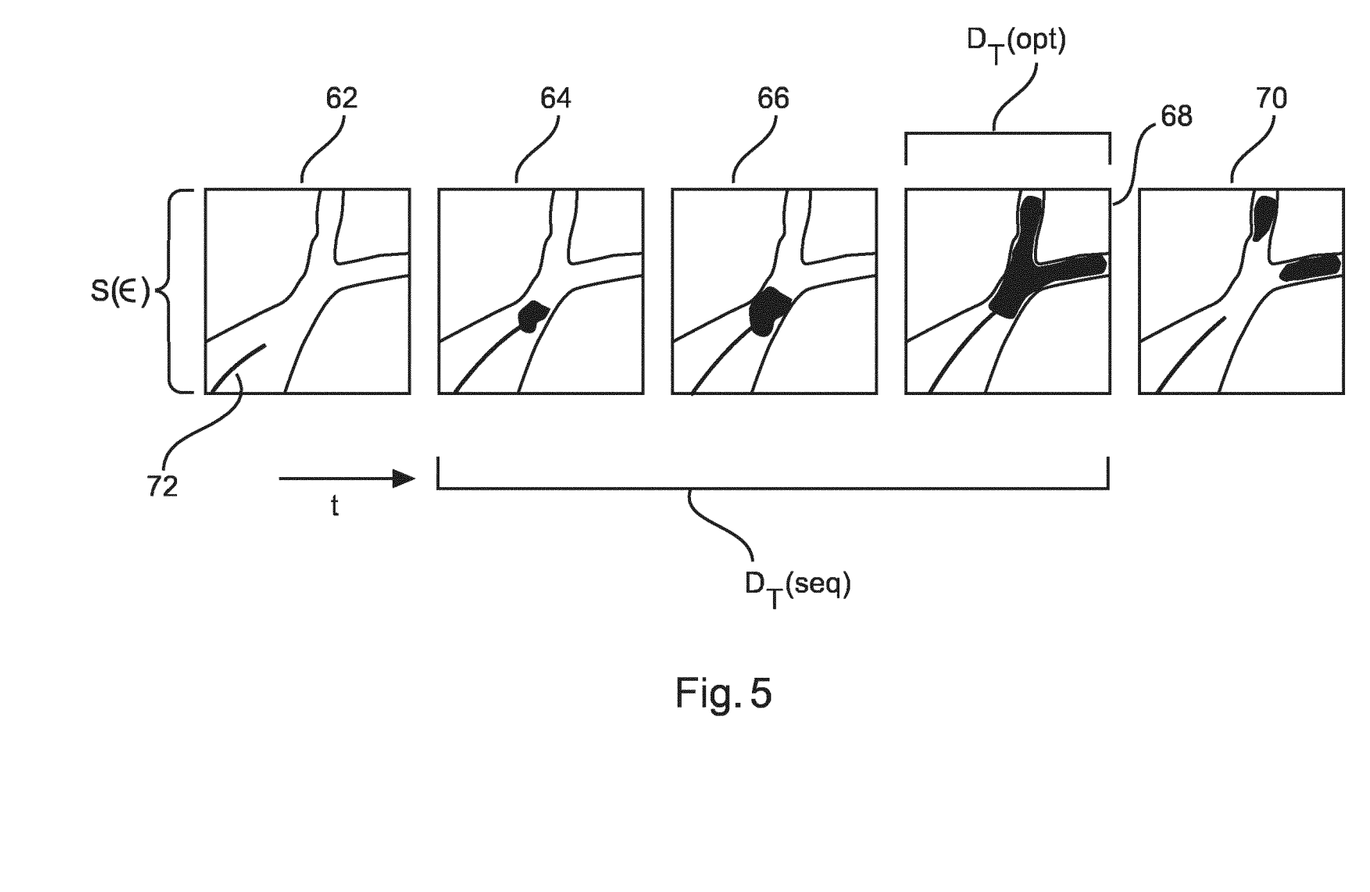
FIG. 5 shows demonstrates an exemplary approach for the selection of frames of a further subset, representing an angiogram.

FIG. 5 illustrates five exemplary frames 62, 64, 66, 68, 70 of an input frame sequence which have been selected as a representative subset $D_T$ of a diagnostic stage of the overall sequence of frames S using contextual information, as described previously. In frame 62, a contrast agent injection catheter 72 is advanced into a vasculature, but no injection has been made. In frame 64, an initial contrast burst is injected into the vasculature. In frame 66, the burst begins to propagate through the vasculature. In frame 68, the burst has spread to the full extent of the vasculature, and provides good quality edges in the angiogram. In frame 70, the burst is beginning to dissipate through the vasculature.

In this example, in the case that one optimal image should be selected from $D_T$, the frames of the sequence $D_T$ would be searched for images providing the highest edge performance between the contrast agent and the surrounding soft tissue, using a ridge filter, for example. Frame 68 would be selected as being the frame having the best edges. In this case, the further subset would be provided as $D_T(opt)$, a single image.

According to an alternative embodiment, an image search operator is provided which enables the detection of the beginning of a contrast burst at frame 64, for example. With knowledge of a frame 64 having the first contrast burst, and the best contrast frame 68, the subset of S, $D_T(seq)$, can be chosen as the further subset being a sequence of frames characterizing a flow of the contrast agent through the vasculature, which may provide a good summary of the diagnostic procedure without using too many redundant frames. Optionally, the subsequent frame 70 may be included to show a perfusion of the contrast agent into the myocardium, for example.

Thus, according to an embodiment, the best-injected sequence from each further subset may be identified. This approach also has wide applicability in situations where sequences are provided for reporting.

Figure 6:
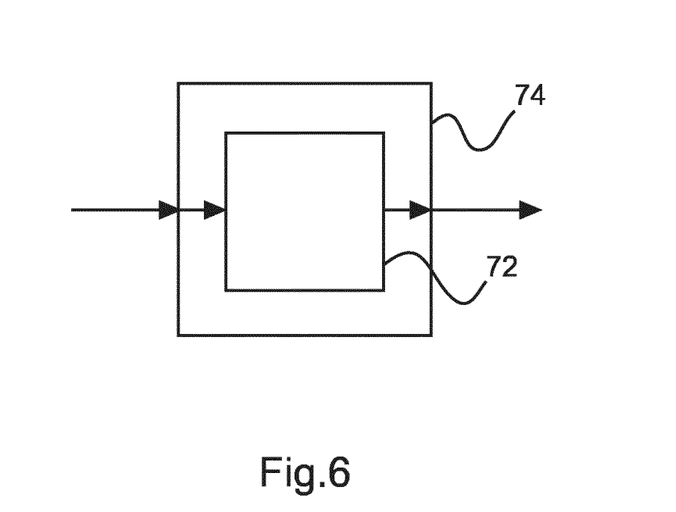
FIG. 6 shows an apparatus according to the first aspect.

According to a first aspect of the invention, there is provided an apparatus 72 for computer-aided medical report provision, comprising:

a processing unit 74.

The processing unit is configured to receive a sequence of frames, obtained from a medical imaging device, representing a region of interest of a patient, to generate contextual information derived from (i) the sequence of frames, and/or (ii) an input from an item of medical equipment. The frames of the sequence of frames are indexed to the contextual information, to generate at least one representative subset of the frames of the sequence of frames.

The frames of the at least one representative subset are selected from the sequence of frames by comparing the contextual information of frames of the sequence of frames to at least one frame clustering condition, selecting at least one further subset of the frames of the at least one representative subset using a selection parameter defined for the at least one representative subset, and outputting a multimedia or documentary report comprising the further subset of frames.

The apparatus 72 according to the first aspect of the invention may, for example, be implemented using a general-purpose computer, a Smartphone, or a tablet computer. Alternatively, the apparatus may be implemented in a general-purpose server in a local area network, on the internet, or as part of a "cloud" processing arrangement. The processing unit 74 may be provided as a Graphics Processing Unit (GPU) or may be implemented in hardware, such as on a Field Programmable Gate Array (FPGA) or on a specialized Digital Signal Processor (DSP).

The apparatus 72 may receive the input sequence of frames, and/or the input from an item of medical equipment, "live" during a medical intervention. Alternatively, the sequence of frames, and its indexed contextual information, may be stored in a data carrier, enabling processing according to aspects of the invention to be performed "offline".

FIG. 6 illustrates the apparatus according to the first aspect.

According to an embodiment of the first aspect, there is provided an apparatus 72 as previously described, wherein the processor 74 is further configured to receive orientation information of an item of medical imaging equipment, wherein the contextual information comprises the orientation information, and wherein the frame clustering condition comprises an orientation condition.

According to an embodiment of the first aspect, there is provided an apparatus 72 as previously described, wherein the processor 74 is further configured to receive an event signal comprising information about an event linked to the stage of a medical procedure, and to generate a procedure status indication using the event signal. The contextual information further comprises the procedure status indication. Frames of the at least one representative subset are selected from the sequence of frames based on the procedure status indication, and the at least one frame clustering condition.

According to an embodiment of the first aspect, there is provided an apparatus 72 as previously described, wherein the event signal is a balloon inflation state signal.

According to an embodiment of the first aspect, there is provided an apparatus 72 as previously described. The processor 74 is further configured to receive a measurement device activity parameter from output signals of a patient monitoring device wherein the contextual information further comprises the measurement device activity parameter, wherein the frames of the at least one representative subset are selected based on the presence of the measurement device activity parameter, and wherein the multimedia or documentary report comprises a measurement from the output signals of a patient monitoring device displayed in proximity to the further subset of frames.

Optionally, the measurement device activity parameter comprises the output of a patient heartbeat monitor. In this way, the contextual information may be synchronized to a patient heartbeat.

Optionally, the measurement device activity parameter comprises the output of a patient breathing monitor. In this way, the contextual information may be synchronized to a patient's breathing cycle.

According to an embodiment of the first aspect, there is provided an apparatus 72 as previously described. The processor 74 is further configured to classify frames of the sequence of frames by identifying a specific artery system represented in the frames, thereby providing frames of the sequence of frames with an artery system classification, wherein the contextual information further comprises the artery system classification, wherein the frame clustering condition comprises an artery system classification parameter, and wherein frames of the at least one representative subset are selected based on a comparison of the artery system classification of each frame with the artery system parameter.

According to an embodiment of the first aspect, there is provided an apparatus 72 as previously described. The processor 74 is further configured to compute a contrast agent quality metric for a plurality of frames of the at least one representative subset of the frames, wherein the selection parameter is an injection quality parameter, and the frames of the at least one further subset of the frames are selected based on a comparison of the contrast agent quality metric and the injection quality parameter.

According to an embodiment of the first aspect, there is provided an apparatus 72 as previously described. The processor is further configured to compute a balloon inflation progress metric for a plurality of frames of the at least one representative subset of the frames, wherein the selection parameter is a balloon inflation extent metric, and wherein the frames of the at least one further subset of the frames are selected based on a comparison of the balloon inflation progress metric and the balloon inflation extent metric.

According to a third aspect of the invention, there is provided a system 10 configured for medical reporting. The system is illustrated in FIG. 1. The system comprises:
 a medical imaging system 14;
 an apparatus 28 according to the previously described first aspect and its embodiments, and
 a display arrangement 29.

The medical imaging system is configured to generate a sequence of frames, and the apparatus is communicatively coupled to the medical imaging system and the display arrangement, and wherein, in operation, the apparatus receives the sequence of frames from the medical imaging system, and outputs a multimedia or documentary report comprising a subset of frames of the sequence of frames.

According to a fourth aspect, a computer program element for medical reporting comprising instructions, which, when the computer program element is executed by a processing unit, is adapted to perform the method steps of the second aspect, or its embodiments.

According to an embodiment of the fourth aspect, the computer program element is provided which is configured to control an apparatus according to the first aspect, or its embodiments.

According to a fifth aspect, a computer-readable medium having stored the program element of the fourth aspect is provided.

A computer program element might therefore be stored on a computer unit, which might also be part of an embodiment of the present invention. This computing unit may be adapted to perform or induce performance of the steps of the method described above.

Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both the computer program that has the invention installed from the beginning, and a computer program that by means of an update turns an existing program into a program that uses the invention. A computer program may be stored and/or distributed on a suitable medium, such as an optical storage media or a solid state medium supplied together with, or as a part of other hardware, but may also be distributed in other forms, such as via the Internet or other wired or wireless telecommunication systems.

However, the program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It should to be noted that embodiments of the invention are described with reference to different subject-matters. In particular, some embodiments are described with reference to method-type claims, whereas other embodiments are described with reference to the device-type claims. However, a person skilled in the art will gather from the above, and the following description, that unless otherwise notified, in addition to any combination of features belonging to one type of subject-matter, also any other combination between features relating to different subject-matters is considered to be disclosed with this application.

All features can be combined to provide a synergetic effect that is more than the simple summation of the features.

While the invention has been illustrated and described in detail in the drawings and foregoing description, such illustration and description are to be considered illustrative or exemplary, and not restrictive. The invention is not limited to the disclosed embodiments.

Other variations to the disclosed embodiments can be understood, and effected by those skilled in the art in practicing the claimed invention, from a study of the drawings, the disclosure, and the dependent claims.

In the claims, the word "comprising" does not exclude other elements or steps, and the indefinite article "a" or "an" does not exclude a plurality. A single processor, or other unit, may fulfil the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. An apparatus, comprising:
 a processor configured to:
  receive an input sequence of frames representing images of a region of interest of a patient, obtained from a C-arm imaging system which includes a C-arm;
  receive an event signal comprising information about an event linked to a stage of a medical procedure and generate a procedure status indication based on the event signal;
  generate contextual information for the input sequence of frames from the C-arm imaging system, wherein the contextual information comprises (a) orientation information obtained from: (i) azimuth and elevation angles of the C-arm, or (ii) an image processing algorithm applied to image content of the input sequence of frames from the C-arm imaging system and (b) the procedure status indication, wherein the frames of the input sequence of frames are indexed to the contextual information;

generate at least one representative subset of frames, from the input sequence of frames, that represents the stage of the medical procedure, wherein the processor is configured to select the frames of each at least one representative subset from the input sequence of frames by comparing the contextual information, which is indexed to the frames of the input sequence of frames, to the procedure status indication and at least one frame clustering condition, wherein the at least one frame clustering condition includes an orientation condition for the C-arm;

select at least one further subset of the frames of the at least one representative subset using a selection parameter defined for the at least one representative subset; and output a multimedia or documentary report comprising the further subset of frames.

2. The apparatus of claim 1, wherein the event signal is a balloon inflation state signal.

3. The apparatus of claim 1, wherein the processor is further configured to:

receive a measurement device activity parameter from output signals of a patient monitoring device, wherein the contextual information further comprises the measurement device activity parameter, wherein the frames of the at least one representative subset are selected based on the presence of the measurement device activity parameter, and wherein the multimedia or documentary report comprises a measurement from the output signals of the patient monitoring device displayed in proximity to the further subset of frames.

4. The apparatus of claim 3, wherein the processor is further configured to:

classify frames of the input sequence of frames by identifying a specific artery system represented in the frames, thereby providing frames of the input sequence of frames with an artery system classification, wherein the contextual information further comprises the artery system classification, wherein the frame clustering condition comprises an artery system classification parameter.

5. The apparatus of claim 1, wherein the processor is further configured to:

compute a contrast agent quality metric for a plurality of frames of the at least one representative subset, wherein the contrast agent quality metric is a measure of how much contrast agent is visible in a frame, and wherein the selection parameter is an injection quality parameter defining a quality of a distribution of the contrast agent in a lumen, and wherein the frames of the at least one further subset are selected based on a comparison of the contrast agent quality metric and the injection quality parameter.

6. The apparatus of claim 5, wherein the processor is further configured to:

compute a balloon inflation progress metric for a plurality of frames of the at least one representative subset, wherein the selection parameter is a balloon inflation extent metric, and wherein the frames of the at least one further subset are selected based on a comparison of the balloon inflation progress metric and the balloon inflation extent metric.

7. The system of claim 1, comprising:
the C-arm imaging system, including the C-arm, and
a display arrangement;
wherein, in operation, the processor receives the input sequence of frames and azimuth and elevation angle signals from the C-arm imaging system.

8. The apparatus of claim 1, wherein the orientation information is the azimuth and elevation angles of a C-arm of the C-arm imaging system, wherein the frame clustering condition is a quadrant of an azimuth and elevation space of the C-arm, and wherein the processor is configured to select the frames of the at least one representative subset from the input sequence of frames by comparing the azimuth and elevation angles of the C-arm to the quadrant.

9. A method, comprising:

receiving an input sequence of frames, obtained from a C-arm imaging system which includes a C-arm, representing images of a region of interest of a patient;

receiving an event signal comprising information about an event linked to a stage of a medical procedure and generate a procedure status indication based on the event signal;

generating contextual information for the input sequence of frames from the C-arm imaging system, wherein the contextual information comprises (a) orientation information obtained from: (i) azimuth and elevation angles of the C-arm, or (ii) an image processing algorithm applied to image content of the input sequence of frames from the C-arm imaging system and (b) the procedure status indication, wherein the frames of the input sequence of frames are indexed to the contextual information;

generating at least one representative subset of frames, from the input sequence of frames, that represents the stage of the medical procedure, wherein the frames of each at least one representative subset are selected from the input sequence of frames by comparing the contextual information, which is indexed to the frames of the input sequence of frames, to the procedure status indication and at least one frame clustering condition, wherein the frame clustering condition comprises an orientation condition for the C-arm;

selecting at least one further subset of the frames of the at least one representative subset using a selection parameter defined for the at least one representative subset; and outputting a multimedia or documentary report comprising the further subset of frames.

10. The method of claim 9, further comprising:
receiving orientation information of the C-arm, including the azimuth and elevation angles of the C-arm;
wherein the contextual information includes the received orientation information; and
wherein the orientation condition comprises an orientation of the C-arm.

11. The method of claim 9, further comprising:
computing a contrast agent quality metric for a plurality of frames of the at least one representative subset;
wherein the selection parameter is an injection quality parameter, and
wherein the frames of the at least one further subset are selected based on a comparison of the contrast agent quality metric and the injection quality parameter.

12. The method of claim 9, wherein the orientation information is the azimuth and elevation angles of a C-arm of the C-arm imaging system, wherein the frame clustering condition is a quadrant of an azimuth and elevation space of the C-arm, and wherein selecting the frames of the at least one representative subset from the input sequence of frames comprises comparing the azimuth and elevation angles of the C-arm to the quadrant.

13. The method of claim 9, wherein the event signal is a balloon inflation state signal.

14. The method of claim 9, further comprising:

receiving a measurement device activity parameter from output signals of a patient monitoring device, wherein the contextual information further comprises the measurement device activity parameter, wherein the frames of the at least one representative subset are selected based on the presence of the measurement device activity parameter, and wherein the multimedia or documentary report comprises a measurement from the output signals of the patient monitoring device displayed in proximity to the further subset of frames.

15. The method of claim 9, further comprising:

classifying frames of the input sequence of frames by identifying a specific artery system represented in the frames, thereby providing frames of the input sequence of frames with an artery system classification, wherein the contextual information further comprises the artery system classification, wherein the frame clustering condition comprises an artery system classification parameter.

16. The method of claim 9, further comprising:

computing a balloon inflation progress metric for a plurality of frames of the at least one representative subset, wherein the selection parameter is a balloon inflation extent metric, and wherein the frames of the at least one further subset are selected based on a comparison of the balloon inflation progress metric and the balloon inflation extent metric.

17. The method of claim 9, further comprising receiving azimuth and elevation angle signals from the C-arm imaging system.

18. A tangible non-transitory computer readable medium having stored thereon instructions of a computer program which, when executed by a processor, cause the processor to:

receive an input sequence of frames, obtained from a C-arm imaging system which includes a C-arm, representing images of a region of interest of a patient;

receive an event signal comprising information about an event linked to a stage of a medical procedure and generate a procedure status indication based on the event signal;

generate contextual information for the input sequence of frames from the C-arm imaging system, wherein the contextual information comprises (a) orientation information obtained from: (i) azimuth and elevation angles of the C-arm, or (ii) an image processing algorithm applied to image content of the input sequence of frames from the C-arm imaging system and (b) the procedure status indication, wherein the frames of the input sequence of frames are indexed to the contextual information;

generate at least one representative subset of frames, from the input sequence of frames, that represents the stage of the medical procedure, wherein the frames of each at least one representative subset are selected from the input sequence of frames by comparing the contextual information, which is indexed to the frames of the input sequence of frames, to the procedure status indication and at least one frame clustering condition, wherein the frame clustering condition comprises an orientation condition for the C-arm;

select at least one further subset of the frames of the at least one representative subset using a selection parameter defined for the at least one representative subset; and output a multimedia or documentary report comprising the further subset of frames.

\* \* \* \* \*